United States Patent
Akinpelu et al.

(10) Patent No.: US 9,023,332 B2
(45) Date of Patent: May 5, 2015

(54) HAIR STYLING COMPOSITION

(75) Inventors: Akinwole Oladiran Akinpelu, Bebington (GB); Prem Kumar Cheyalazhagan Paul, Bebington (GB); Christopher John Roberts, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 14 days.

(21) Appl. No.: 13/983,859

(22) PCT Filed: Feb. 3, 2012

(86) PCT No.: PCT/EP2012/051891
§ 371 (c)(1),
(2), (4) Date: Sep. 12, 2013

(87) PCT Pub. No.: WO2012/107366
PCT Pub. Date: Aug. 16, 2012

(65) Prior Publication Data
US 2013/0344020 A1     Dec. 26, 2013

(30) Foreign Application Priority Data

Feb. 9, 2011   (EP) .................................. 11153793

(51) Int. Cl.
*A61Q 5/06* (2006.01)
*A61K 8/81* (2006.01)

(52) U.S. Cl.
CPC ............. *A61K 8/8188* (2013.01); *A61K 8/8152* (2013.01); *A61K 8/8158* (2013.01); *A61Q 5/06* (2013.01); *A61K 8/817* (2013.01)

(58) Field of Classification Search
None
See application file for complete search history.

(56) References Cited

U.S. PATENT DOCUMENTS

| 5,166,276 A | 11/1992 | Hayama et al. |
| 7,048,916 B2 | 5/2006 | Rollat et al. |
| 2001/0022967 A1 | 9/2001 | Brandt et al. |
| 2007/0140991 A1 | 6/2007 | Maitra et al. |
| 2009/0071495 A1 | 3/2009 | Nguyen et al. |
| 2013/0344017 A1 | 12/2013 | Chandra et al. |
| 2013/0344020 A1 | 12/2013 | Akinpelu et al. |

FOREIGN PATENT DOCUMENTS

| EP | 0412707 A1 | 2/1991 |
| EP | 0408311 B1 | 10/1996 |
| EP | 0412704 B1 | 4/1999 |
| EP | 1084695 A1 | 3/2001 |
| FR | 2924339 A1 | 6/2009 |
| FR | 2924339 T | 6/2009 |
| JP | 2006069903 | 3/2006 |
| WO | WO2004037217 A1 | 5/2004 |
| WO | WO2007071308 A1 | 6/2007 |
| WO | WO2008012733 A2 | 1/2008 |
| WO | WO2009118253 A2 | 10/2009 |

OTHER PUBLICATIONS

PCT International Search Report in PCT application PCT/EP2012/051891 dated Mar. 8, 2012 with Written Opinion.
European Search Report in EP application EP 11 15 3793 dated Jul. 19, 2012.
PCT International Search Report in PCT application PCT/EP2012/051893 dated Mar. 8, 2012 with Written Opinion.
European Search Report in EP application EP 11 15 3795 dated Jul. 20, 2011.
Co-pending Application: Applicant: Akinpelu et al., U.S. Appl. No. 13/983,801, filed Sep. 12, 2013.
PCT International Search Report in PCT application PCT/EP 2012/051892 dated Mar. 8, 2012 with Written Opinion.
European Search Report in EP application EP 11 15 3794 dated Jul. 19, 2011.
Co-pending Application: Applicant: Akinpelu et al., U.S. Appl. No. 13/983,842, filed Sep. 12, 2013.

*Primary Examiner* — Jyothsna Venkat
(74) *Attorney, Agent, or Firm* — Ronald A. Koatz

(57) ABSTRACT

A hair treatment composition comprising: i) a polyacrylate cross polymer; and ii) an acrylic pressure sensitive adhesive comprising: a) an acrylic group having a side-chain with at least 4 carbons (eg n-butyl acrylate or 2-ethylhexyl acrylate) and; b) a short side-chain acrylic such as methyl acrylate.

4 Claims, No Drawings

HAIR STYLING COMPOSITION

This invention relates to hair treatment compositions and to their use in the treatment of hair.

Pressure sensitive adhesives (PSAs) have been used in hair care compositions as described in U.S. Pat. No. 5,166,276, EP408311, EP412707 and EP412704. However these PSAs tend to hydrolyse in aqueous and hydro/alcoholic hair care products.

WO2007/071308 discloses compositions comprising pressure sensitive adhesives having superior foaming properties.

WO2004/037217 describes heat activated durable styling compositions comprising saccharides and film forming agents.

WO 2008/012733 discloses compositions for permanently shaping hair. The composition comprises a N-alkyl-2-mercaptoacetamide as the active agent and a range of swelling and penetration enhancement agents including maltotriose.

The present invention concerns hair care compositions which impart re-styling benefits to the hair and are stable.

DESCRIPTION OF THE INVENTION

Accordingly in a first aspect the present invention relates to a hair care composition comprising:
  i) a polyacrylate cross polymer; and
  ii) an acrylic pressure sensitive adhesive comprising:
    a) an acrylic group having a side-chain with at least 4 carbons (eg n-butyl acrylate or 2-ethylhexyl acrylate) and;
    b) a $C_1$-$C_6$ side-chain acrylic such as methyl acrylate.

The invention further relates to a method of styling hair comprising the steps of application of the above described composition to the hair.

DETAILED DESCRIPTION OF THE INVENTION

In the context of the present invention stable compositions relate to compositions that do not agglomerate or congeal on storage. Typical storage conditions are room temperature (20° C. for a week), preferably a month.

Pressure Sensitive Adhesives

Compositions of the invention comprise an acrylic pressure sensitive adhesive.

"Pressure sensitive adhesive" (PSA) materials are permanently tacky at room temperature and able to develop measurable adhesion to a surface simply upon contact or by the application of a light pressure. Generally they do not require heat. No chemical reaction takes place between the adhesive and the adherent, no curing of the adhesive is necessary and no solvent is required to be lost during the adhesion process.

The acrylic PSAs of the invention are random copolymers comprising:
  i) an acrylic group having a side-chain with at least 4 carbons (eg n-butyl acrylate or 2-ethylhexyl acrylate), and;
  ii) a $C_1$-$C_6$ side-chain acrylic such as methyl acrylate.

The weight ratio of short side chain acrylic group ii) to the acrylic group i) is from 1.9:98.1 to 4.0:96.0, preferably from 1.9 to 98:1 to 2.5:97.5.

It is preferable if the copolymer does not include acrylic acid.

It is preferable if the molecular weight (Mn) of the copolymer is from $8 \times 10^4$ to $1 \times 10^4$, preferably from $6 \times 10^4$ to $2 \times 10^4$.

Small molecule additives such as tackifiers may be included, essentially to adjust the Tg and optimise dissipative properties but are not essential.

The acrylic sensitive pressure adhesive is preferably in the form of an emulsion. Suitable water-born acrylic sensitive pressure adhesives include Roderm MD-5800 ex Rohm and Haas.

Preferably the acrylic pressure sensitive adhesive is present at levels from 0.01% to 10% by weight of the total composition. More preferred amounts of acrylic pressure sensitive adhesive in the compositions of the invention are from 0.1% to 5% by weight of the composition, even more preferably from 0.5% to 3.5% by weight.

Polyacrylate Crosspolymer

Compositions of the invention comprise a polyacrylate crosspolymer, preferably this polymer is a copolymer comprising ammonium 2 acrylamido 2 methyl propane sulphonate, most preferably it is polyacrylate crosspolymer-6 (a copolymer of ammonium acryloyldimethyltaurate, dimethylacrylamide, lauryl methacrylate and laureth-4 methacrylate, crosslinked with trimethylolpropane triacrylate).

The level of polyacrylate present in the total composition is from 0.05 wt % to 10 wt %, more preferably from 0.2 wt % to 5 wt %, most preferably from 0.5 wt % to 4 wt %.

Preferably the ratio of polyacrylate crosspolymer to acrylic PSA is from 0.5:5 to 2:1, more preferably from 1:1 to 1:4.

Further Styling Polymers

In some aspects of this invention it is highly desirable if the composition further comprises an additional styling polymer.

Particularly useful as styling aids with this invention are hair styling polymers. Hair styling polymers are well known articles of commerce and many such polymers are available commercially which contain moieties which render the polymers cationic, anionic, amphoteric or nonionic in nature. The polymers may be synthetic or naturally derived.

Styling aids such as vinylic polymer are preferred, in particular block copolymers.

The amount of the hair styling polymer may range from 0.1 to 10%, preferably 0.5 to 8%, more preferably 0.75 to 6% by weight based on total weight of the composition.

Product Format

Compositions of the present invention are formulated into hair care compositions with hair styling claims. The compositions are preferably used to non-permanently style human hair and, more preferably, they are packaged and labeled as such. The term non-permanently mean that during the styling process the inter cystine-disulphide bonds are not broken. This means that there are no reductive agents in the hair care composition.

It is preferred if the products are left on hair after application and not immediately washed off (within 1 hour of application). Such products are known as leave in compositions.

Preferred product forms are leave on formulations such as gels, waxes and creams.

Alternative styling forms include mousses, sprays and aerosols.

Such styling products frequently include a carrier and further additional components. The carriers and additional components required to formulate such products vary with product type and can be routinely chosen by one skilled in the art. The following is a description of some of these carriers and additional components.

Further Ingredients

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such glycine/sodium hydroxide, citric acid, lactic acid, succinic acid, acetic salt and salts thereof. Frequently a mixture of buffering system is used such as sodium citrate and citric acid.

Carriers suitable for use with hair care compositions of the present invention include, for example, those used in the formulation of hair sprays, mousses, tonics, waters, creams gels, shampoos, conditioners, and rinses. The choice of appropriate carrier will depend on the particular product to be formulated. The carriers used herein can include a wide range of components conventionally used in hair care compositions. The carriers can contain a solvent to dissolve or disperse the styling compound being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling waxes, creams or gels also typically contain a structurant or thickener, typically in an amount of from 0.01% to 10% by weight.

Suitable spray containers are well known in the art and include conventional, non-aerosol pump sprays i.e., "atomisers", aerosol containers or cans having propellant, as described above, and also pump aerosol containers utilising compressed air as the propellant.

The formulation may include conditioning materials such as surfactants, cationic conditioners suitable for hair, quaternary silicone polymers, silicone based conditioners and their emulsions, and amino functional silicones and their emulsions.

Further general ingredients suitable for all product forms include, sun-screening agents, anti-dandruff actives, carboxylic acid polymer thickeners for hair shampoo and conditioner compositions and emulsifiers for emulsifying the various carrier components of the compositions of the invention.

The compositions of the present invention may also contain adjuncts suitable for hair care. Generally such ingredients are included individually at a level of up to 2, preferably up to 1 wt % of the total composition. Suitable hair care adjuncts, include amino acids, sugars and ceramides.

The method of the invention comprises applying compositions of the invention preferably followed natural or fan assisted drying only.

The following non-limiting Examples further illustrate the preferred embodiments of the invention. All percentages referred to in the examples and throughout this specification are by weight based on total weight unless otherwise indicated.

EXAMPLES

Experiment 1

The following base formulations were prepared:

TABLE 2

Comparative Examples- Base 1

| Trade Name | Chemical (INCI) Name | Supplier | % Active | % W/W |
|---|---|---|---|---|
| Roderm MD5800 | 98% ButylAcrylate (BA), 2% MethylAcrylic Acid (MAA) | Rohm & Haas | 57 | 0 to 2 |
| Tinovis CD | Dimethylacrylamide/ Ethyltrimonium Chloride Methacrylate Copolymer and Propylene Glycol Dicaprylate/Dicaprate and PPG-1 Trideceth-6 and C10-11 Isoparaffin | CIBA | 50 | 0.10 |
| | Water and minors | | | To 100 |

TABLE 3

Examples according to the invention - Base 2

| Trade Name | Chemical (INCI) Name | Supplier | % Active | % W/W |
|---|---|---|---|---|
| Roderm MD5800 | 98% ButylAcrylate (BA), 2% MethylAcrylic Acid (MAA) | Rohm & Haas | 57 | 0 to 5 |
| Sepimax Zen | Polyacrylate crosspolymer-6 | Seppic | 100 | 1.0 |
| | Water and minors | | | To 100 |

The stability of the above formulations having different levels of MD5800 are given below.

TABLE 4

| MD-5800 Concentration | Comparative Base 1 | Example Base 2 |
|---|---|---|
| 1% | Unstable | Stable |
| 2% | Unstable | Stable |
| >2% | Unstable | Stable |

Un-stable—agglomerated particles within composition or congealed product.

Experiment 2

Using the base formulation above the restylability of hair treated with the formulations was assessed as follows:

Dark brown wavy switches (25 cm and 2 gm in weigh) were washed and conditioned in Sunsilk (Lively clean and fresh). The wet switches were combed through and 0.35 gm of aqueous solution containing the treatment polymer was applied to each switch and massaged through. The switches were dried and ironed straight and were placed in an image analysis chamber at 30 C and 80% RH and agitated for a further 30 minutes. The volumes of the switches were captured at initial and after the 30 minute time point. Due to the high humidity and agitation the switches would have fluffed up—displaying a loss of style. Subsequently the switches were restyled by combing 5 times and squeezing between fingers and thumb and running over the switch 5 times. The volume after restyling was also captured.

If V0 is the initial straight ironed volume, V1 the volume after 30 minutes of high humidity and agitation and V2 the volume after restyling, then $$\text{Restyling index} = (V1-V0)*100/(V1-V2)$$

TABLE 5

| formulation | % restylability |
|---|---|
| Base 2 | −15.08 |
| 1% MD5800 in Base 2 | 16.56 |
| 3% MD5800 in Base 2 | 30.26 |
| 5% MD5800 in Base 2 | 52.74 |

From the table above it can be seen that formulations of the invention when applied to the hair confer a restyling benefit to the hair.

The invention claimed is:

1. A hair treatment composition consisting of:
   i) polyacrylate crosspolymer-6, wherein the polyacrylate crosspolymer-6 is from 0.2 to 5 wt % of the total composition;
   ii) an acrylic pressure sensitive adhesive, wherein the an acrylic pressure sensitive adhesive is 98% butyl acrylate and 2% methylacrylicacid; and
   iii) water.

2. A hair treatment composition according to claim 1 that is a cream, gel or wax.

3. A hair treatment composition according to claim 1 that is a leave in composition.

4. A method of non-permanently styling hair comprising the step of applying to the hair a hair composition according to claim 1.

* * * * *